United States Patent [19]

Maxim et al.

[11] Patent Number: 4,883,813

[45] Date of Patent: Nov. 28, 1989

[54] METHOD OF TREATING INFLAMMATION IN MAMMALS UTILIZING KETOBUTYROLACTONES AND FURYLBUTYROLACTONES

[75] Inventors: Peter E. Maxim, Germantown; Robert W. Veltri, Gaithersburg, both of Md.

[73] Assignee: American Biotechnology Company, Rockville, Md.

[21] Appl. No.: 236,003

[22] Filed: Aug. 24, 1988

[51] Int. Cl.⁴ .............................................. A61K 31/34

[52] U.S. Cl. ................................................... 514/470
[58] Field of Search ......................................... 514/470

Primary Examiner—Stanley J. Friedman
Attorney, Agent, or Firm—Wyatt, Gerber, Burke and Badie

[57] ABSTRACT

Treatment of inflammation in mammals utilizing selected ketobutyrolactones and furylbutyrolactones. Treatment is applicable to both acute or chronic inflammation. Antiviral activity of methylfurylbutyrolactone is also disclosed.

11 Claims, No Drawings

METHOD OF TREATING INFLAMMATION IN MAMMALS UTILIZING KETOBUTYROLACTONES AND FURYLBUTYROLACTONES

This invention is concerned with the use of certain known ketobutyrolactones and furylbutyrolactones in the treatment of inflammation, both acute and chronic, and with the antiviral activity of one of them.

Inflammation is caused by the release of chemicals from tissues and migrating cells. It covers a host of pathophysiological events, and occurs as both acute and chronic conditions. Acute inflammation is usually associated with trauma such as infection, invasion by foreign bodies, surgery, radiotherapy and the like. Chronic inflammation occurs with physiological conditions such as asthma, hay fever, periodontitis, arthritis, and environmental reactions such as poison ivy, nettle rash and other forms of dermatitis.

A host of therapeutic agents both steroidal and non-steroidal are available for treating inflammatory conditions including aspirin, indomethacin, dexamethasone, phenylbutazone, colchicine, and others. They work by a variety of mechanisms, and none is completely satisfactory. There is room for improvement.

It has now been discovered that certain reaction products of ascorbic acids and selected carbonyl compounds, both aliphatic and cyclic are useful to treat both acute and chronic inflammation in mammals including man, horses, dogs and other domestic animals. These compounds are referred to generically in this disclosure as furylbutyrolactones and ketobutyrolactones.

The furylbutyrolactones which can be used in the practice of this invention include those represented by the formula:

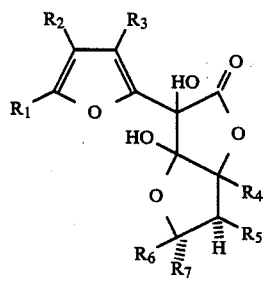

wherein $R_1$, $R_2$, $R_3$, $R_4$, $R_5$ and $R_6$ are selected from the group consisting of hydrogen and lower alkyl which may be the same or different:

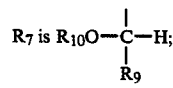

$R_9$ is selected from the group consisting of:

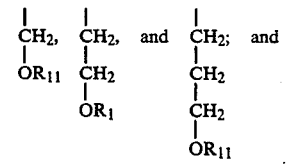

$R_{10}$ and $R_{11}$, which may be the same or different, are selected from the group consisting of hydrogen, lower alkyl, phenyl and hydroxyl substituted lower alkyl.

These compounds are prepared by reacting the corresponding 2,3-dihydroxybutenolides and 2,5-dihydroxy-2,5-dihydrofurans in aqueous solvents at ambient temperature (20° C. to 45° C.) for about 15 to 30 minutes as described in U.S. Pat. No. 4,620,014.

The products can be prepared and, if desired, converted to the corresponding succinic anhydride, succinimide and N-methyl succinimide complexes by the procedures illustrated in Examples 1, 2 and 3 herein.

By far the most preferred compounds of this series are:

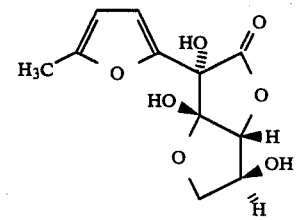

and the corresponding demethyl compound referred to herein as MFBL (methylfurylbutyrolactone) and FBL (furylbutyrolactone) respectively. These compounds are relatively easy to prepare from readily available starting materials, and they are highly effective.

Additional compounds useful in the practice of this invention are represented by the formula:

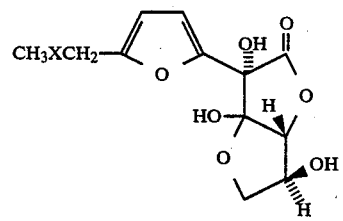

wherein X is sulfur or oxygen.

These compounds are referred to herein as MTMFBL (methylthiomethylfurylbutyrolactone) when X is sulfur and MMFBL (methoxymethylfurylbutyrolactone) when X is oxygen. They are prepared by reaction between ascorbic acid, which is a 2,3-dihydroxybutenolide, by the process described above, described in more detail in copending and commonly assigned patent application Ser. No. 226,685, filed July 28, 1988 and specifically illustrated in Examples 4 and 5 hereof.

Ketobutyrolactones useful in the practice of this invention are represented by the formulas:

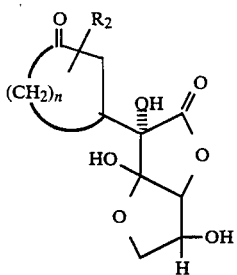

and

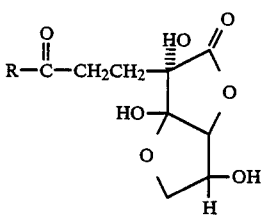

wherein R is lower alkyl and n is 2, 3, or 4 and $R_2$ is hydrogen, lower alkyl or lower haloalkyl.

The preferred compounds of this class within the scope of the invention because of ease of preparation, availability of starting materials and degree of activity are:

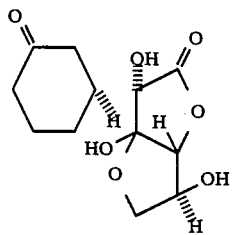
KCBL-A

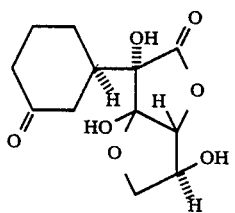
KCBL-B

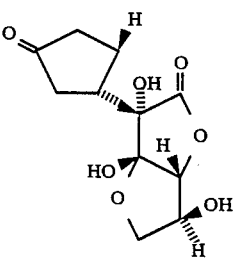
KCPBL-A

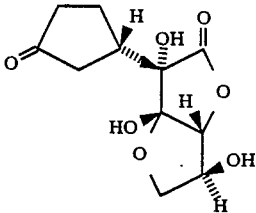
KCPBL-B

It will be seen that the four compounds are in fact two pairs of diasteriosomers. They are, respectively 2-(3-ketocyclohexyl)-2-hydroxy-3-keto-4-dihydroxyethyl butyrolactone <3,6> cyclohemiketal (KCBL) and 2-(3-ketocyclopentyl)-2-hydroxy3-keto-4-dihydroxyethyl butyrolactone <3,6>cyclohemiketal (KCPBL).

This type of product may be prepared by a Michael addition reaction between ascorbic acid and an appropriate α, β-unsaturated alicyclic ketone or vinyl aliphatic ketone as described in copending and commonly assigned application (Docket 17917B) and as specifically illustrated in Examples 6, 7 and 8 hereof.

The reaction is carried out in an aqueous medium at a temperature of about 20° to 40° for 2 to 48 hours in the presence of a catalytic amount of a strong inorganic or organic acid, suitably a mineral acid such as sulfuric or a halogen acid, preferably hydrochloric acid. Preferably the reaction is conducted in an inert atmosphere such as nitrogen or helium.

Those skilled in the art will recognize that several stereoisomers of the compounds used in this invention may exist. The most obvious are those based on L- and D-ascorbic acid. However, as is known, further isomers of each of these isomers also exist, i.e. the 5-isoasorbic acids. So far as is known all isomers of the compounds have some activity, although certain of them are undoubtedly more active than others as is usually the case with naturally occurring physiologically active substance. As a practical matter, it is normally most convenient to synthesize the compounds of the invention without separation of stereoisomers and to utilize the stereoisomeric mixtures so produced. As will be seen in the examples, in at least some instances, it is not exceedingly difficult to separate some stereoisomers within the scope of the invention. Applicants herein have followed the conventional practice in the specification and claims, i.e. unless specifically described or claimed the formulas employed include the sterioisomeric modifications.

It will be understood from a consideration of the preferred compounds within the scope of the above formulas that the preferred R-values are methyl or hydrogen. Lower alkyl substituted products, i.e., alkyl up to about 4 carbon atoms are useful, but generally more difficult and expensive to prepare.

The activity of the compounds used in this invention against acute inflammation is assayed by the art recognized arachidonic acid mouse ear edema assay. In the assay, mice are randomly assigned to groups and are treated intraperitoneally or orally with either potential anti-inflammatory agents (test compounds) positive controls or with drug vehicle.

One hour following injection, the animals are treated on the inner and outer surfaces of the ear with arachidonic acid at a concentration of 2 mg per ear; 30 minutes later the mice are sacrificed by cervical dislocation and ear punches taken of the arachidonic acid and acetone control treated ears. The weights of the punches are recorded to the nearest milligram. Percent change in ear plug weight is calculated:

$$= \frac{(AAc - Vc) - (AAt - Vc)}{(AAc - Vc)} \times 100$$

AAc = Arachidonic acid control
Vc = Vehicle (acetone and buffer controls)
AAt = Arachidonic acid challenged but treated Table I shows the results of this test with various agents of this invention.

The ability of the compounds used in this invention to control chronic inflammation is established by the delayed cutaneous hypersensitivity (DCH) test, an art recognized measure of this therapeutic activity. In the test, mice are immunized to the chemical 4-ethoxymethylene-2-phenyl-oxazol-5-one (oxazolone) by single or multiple applications of 100 ul of a 3% (30 mg/ml) solution in acetone. Ten to 14 days later, mice that had been immunized are challenged by the application of a 1% solution of oxazolone in acetone to the outer surface of the ear. Control animals are challenged with acetone only.

The immune response of the animals to oxazolone is

TABLE I

| AA Induction (topical) | Test Agent (Dose, Volume) | EXPERIMENT 1 30 minutes post-AA Application Ear Plug Weight (mg) | % Inhibition | EXPERIMENT 2 30 minutes post-AA Application Ear Plug 2 (mg) | % Inhibition |
|---|---|---|---|---|---|
| — | — | 13.0 ± 0.9 | — | — | — |
| — | BBS, 0.2 ml | 12.6 ± 1.1 | — | 14.2 ± 0.8 | — |
| AA, 2 mg | BBS, 0.2 ml | 29.6 ± 2.1 | — | 28.2 ± 1.9 | — |
| AA, 2 mg | KBBL, 25 mg/kg, 0.2 ml | NT NT | NT | 27.5 ± 1.0 | 5.0 |
| AA, 2 mg | KBBL, 50 mg/kg, 0.2 ml | 24.8 ± 2.4* | 28.2 | 26.0 ± 1.3*** | 15.7 |
| AA, 2 mg | KBBL, 100 mg/kg, 0.2 ml | 24.2 ± 2.3** | 31.8 | 26.0 ± 1.9*** | 15.7 |
| AA, 2 mg | KBBL, 200 mg/kg, 0.2 ml | 28.8 ± 2.6 | 4.7 | NT NT | NT |
| AA, 2 mg | MFBL, 50 mg/kg, 0.2 ml | 29.6 ± 1.5 | 0.0 | 27.3 ± 1.4 | 6.4 |
| AA, 2 mg | MFBL, 100 mg/kg, 0.2 ml | 26.6 ± 1.1*** | 17.6 | 27.0 ± 2.4 | 8.6 |
| AA, 2 mg | MFBL, 200 mg/kg, 0.2 ml | 23.8 ± 2.7** | 34.1 | 27.0 ± 1.4 | 8.6 |
| AA, 2 mg | MFBL, 400 mg/kg, 0.2 ml | NT NT | NT | 21.5 ± 1.0**** | 47.9 |

*P > 0.009
**P > 0.005
***p > 0.05
****p > 0.0005
N = 5, results = mean ± S.D.
drug = 60 minutes prior to AA, p.o.
NT = Not tested
BBS = bicarbonate buffered saline at pH 6.8

Table II shows the results with MMFBL in third experiment.

TABLE II

| Treatment (mg/kg) | N | AA | Ear Weight (mg) | % INHIBITION |
|---|---|---|---|---|
| Experiment #1 | | | | |
| Saline, 0.2 ml | 48 | (−) | 8.9 +/− 0.26 | (−) |
| Saline, 0.2 ml | 22 | + | 17.6 +/− 0.98 | (−) |
| MMFBL-400 | 8 | + | 15.1 +/− 3.4 | 30 |
| MMFBL-200 | 8 | + | 16.0 +/− 1.2 | 17 |
| Experiment #2 | | | | |
| MMFBL-400 | 5 | + | 13.4 +/− 3.8 | 52 |
| MMFBL-200 | 5 | + | 15.5 +/− 2.4 | 27 |
| Experiment #3 | | | | |
| MMFBL-400 | 5 | + | 16.5 +/− 3.1 | 19 |
| MMFBL-200 | 5 | + | 17.5 +/− 2.7 | 7 |

N = number of animals measured as swelling of the ear with a caliper and can be recorded as an increase in ear thickness measured as ear thickness units (ETU).

Anti-inflammatory response can be measured as a decrease in swelling of the challenged ear after treatment of the mice with test drug.

Percent inhibition of the DCH response is calculated as follows:

$$+ \frac{(Oc - Vc) - (Ot - Vc)}{(Oc - Vc)} \times 100$$

Oc = Oxazolone control
Vc = Vehicle control
Ot = Oxazolone challenged, drug treated Table III shows the activity of certain of the ketobutyrolactones used in this invention as measured by this test. Table IV shows the results with furylbutyrolactones.

TABLE III

| Group | Drug | Dose (mg/kg) | Ox | Ear Thickness (ETU) 8 hr. | % Inhibition | EAR Thickness (ETU) 24 hrs. | % Inhibition |
|---|---|---|---|---|---|---|---|
| | none | — | — | 25.0 ± 2.0 | | 25.0 ± 2.0 | |
| 1 | none | — | + | 37.0 ± 4.5 | | 46.0 ± 4.2 | |
| 2 | KBBL | 200 | + | 31.7 ± 2.6 | 44.2% | 39.2 ± 3.8 | 32.4% |
| 3 | KCBL-A | 200 | + | 29.2 ± 4.9 | 65.0% | 36.7 ± 6.1 | 44.3% |
| 4 | KCBL-B | 200 | + | 32.5 ± 5.2 | 37.5% | 42.5 ± 2.7 | 16.7% |
| 5 | KCPBL-A | 200 | + | 25.8 ± 2.0 | 95.8% | 32.5 ± 4.2 | 64.3% |
| 6 | KCPBL-B | 200 | + | 29.2 ± 2.0 | 65.0% | 44.2 ± 4.9 | 8.6% |
| 7 | D-iso KBBL | 200 | + | 27.0 ± 2.7 | 83.3% | 42.0 ± 5.7 | 19.0% |

TABLE IV

| Group | Drug | Dose (mg/kg) | Ox | Ear Swelling (ETU) Time (hours) 8 hr. | % Inhibition | 24 hrs. | % Inhibition |
|---|---|---|---|---|---|---|---|
| | | | | Experiment 1 | | | |
| 1 | none | — | — | 25.0 ± 2.0 | | 26.4 ± 2.4 | |
| 2 | none | — | + | 32.0 ± 2.7 | | 34.0 ± 4.2 | |
| 3 | D-isoFBL | 200 | + | 26.7 ± 2.6 | 75.7% | 30.0 ± 2.0 | 52.6% |
| 4 | D-isoMFBL | 200 | + | 25.8 ± 2.0 | 88.6% | 30.0 ± 3.2 | 52.6% |
| 5 | FBL | 200 | + | 27.5 ± 2.7 | 64.3% | 29.2 ± 2.0 | 63.23% |
| 6 | MethoxyMFBL | 200 | + | 25.0 ± 2.0 | 100.0% | 26.7 ± 2.6 | 96.1% |
| 7 | MFBL | 200 | + | 25.8 ± 2.0 | 88.6% | 26.7 ± 2.6 | 96.1% |
| 8 | Methylthio MFBL | 200 | + | 29.4 ± 4.2 | 37.1% | 33.0 ± 4.5 | 13.2% |
| | | | | Experiment 2 | | | |
| 1 | none | — | + | 37.5 ± 2.7 | | 52.5 ± 4.2 | |
| 2 | MFBL-S | 200 | + | 38.8 ± 2.5 | | 48.8 ± 2.5 | 14.2% |
| 3 | MFBL-SA | 200 | + | 36.3 ± 4.8 | 9.6% | 48.8 ± 2.5 | 14.2% |

MFBL-S in the N—methyl succinimide complex of MFBL and MFBL-SA is the succinic anhydride complex. See Examples 1 and 3.

MFBL, one of the compounds of this invention has been found to exhibit antiviral activity, particularly against retroviruses.

The retroviruses are a broad group of RNA viruses which during their replication employ the reverse transcription enzyme (RT) to convert an RNA message to DNA. The retroviridae family of viruses includes Lentiviruses (visna, Maedi, progressive pneumonia virus-"slow viruses"), Spumaviruses (foamy viruses) and Oncovirus (types A, B, C, D, RNA tumor viruses). The retroviruses have been shown to infect murine, avian, feline, primate, and human species.

The human immunodeficiency virus (HIV) or human T-cell lymphotropic virus (HTLV-III) which causes Acquired Immune Deficiency Syndrome (AIDS), AID related complex (ARC), and AIDS related diseases is a retrovirus. Also, the feline leukemia virus (FeLV) of cats is a retrovirus.

MFBL was tested against feline leukemia virus by the Sidewell and Huffman procedure using the 81C cell line as the target. The 81C cell is a feline kidney cell transformed with a murine leukemia virus. (ras gene +). The compound was found to have an inhibitory effect against the virus at a concentration well below the toxicity level.

The compound was also tested against the human immunodeficiency virus, HTLV-III according to the following protocol:

1. Target cells are ATH8 cells, a tetanus toxoid antigen specific cytotoxic T-cell clone transformed to a cell line with HTLV-I. The cell line produces a specific cytopathic effect when infected with HIV (HTLV-III).
2. Virus source-HTLV-III from 48 hour infected H9 T-cell line culture supernatants.
3. Protocol:
   (a) ATH8 cells are treated with polybrene (2 ug/ml) for 30' at 37° C.
   (b) Cells are collected by centrifugation to remove polybrene.
   (c) Above cells are then resuspended in freshly harvested and clarified medium containing HTLV-III (about 200–500 virus particles/cell).
   (d) After a 60' adsorption of virus to cells (2×10⁴ cells) at 37° C., 0.1 nl of the virus and cell suspension (containing 2×10⁴ cells) are added to triplicate wells of a 96 well tissue culture plate.
   (e) 0.1 of the test compound is then added to each well and the plates are incubated at 37° C. The cytopathic effects are determined between day 11 and 14 post-virus innoculation by removing 15 ul samples of resuspended cells from selected wells, mixing with 15 ul of trypan blue dye and examined microscopically for cell number and viability.

In two separate runs of this test, the compound was found to have a therapeutic index of greater than 100. This should be compared with a therapeutic indices of 32 and 100 in the same tests for 3'-azido-3'deoxythymidine (AZT), the presently approved drug of choice for treating AIDS. The therapeutic index is the quotient of the 50% inhibitory dose divided by the minimal toxic concentration.

The antiviral activity of the compounds of this invention appears to be a two pronged attack. There is direct antiviral activity as with conventional antiviral agents. There is also the added factor of immunostimulation to marshal the body's natural defenses against viruses or any other foreign agent.

The biologically active compounds of this invention may be administered in effective amounts, alone or in combination with acceptable pharmaceutical carriers, the choice of which is determined by the preferred route of administration, the solubility of the compound, the effect desired and standard pharmaceutical practice.

Oral and parenteral dosage units will be prepared in accordance with standard procedures and will contain the selected active compound as the only or principal active ingredient in the composition. Any of a wide variety of known inert excipients may be employed to prepare useful compositions. These include, for example, dextrose, starch, talc, various types of clay, mineral oil, cottonseed or sesame oil, as well as water or various miscible and immiscible aqueous compositions in which the therapeutic agent is soluble or may be suspended with the aid of known surfactants.

For buccal and sublingual administration, the active ingredient can be formulated in tablet form with water soluble binding agents such as lactone or other palatable carbohydrates.

For rectal administration, suppositories or inserts containing the active ingedient dispersed in such reagents as cocoa butter, petrolatum, or other natural lubricants or in a synthetic emmollient such as polyethylene glycol 1000 or polyethylene glycol 4000 may be used.

It is convenient to administer the active agents of this invention from sustained release dosage forms. This avoids the necessity of constant clock watching or interruption or normal daily activities. A number of compositions suitable for such preparations are known and can be usefully employed.

For oral, sustained release administration, the selected therapeutic agent may be in a time disintegrating tablet or pellet coated with various thickness of known materials such as carnauba wax, cellulose esters and ethers, fats, keratin, gluten or various natural or synthetic esters. Tablets in which the selected agent is contained in a slowly dissolving core such as a core of stearic acid or castor oils are useful. Mixed release granule tablets comprising mixtures of the drug itself and the drug in separate particles coated with materials which dissolve at different rates such as dehydrogenated castor oil or fatty acids can also be employed. Alternatively the active material can be bound to an ion exchange resin such as a sulfuric acid type cation exchange resin.

A number of transdermal formulations are possible for use in the practice of this invention. They are discrete dosage forms in construction systems which, when applied to the skin deliver the therapeutic agent through the skin at a controlled rate for systemic circulation. The system typically comprises an outer covering barrier, a drug reservoir which may have a rate of release controlling membrane, a contact adhesive applied to some or parts of the system at the system/skin interface and a protective layer which is removed before applying the system.

The drug reservoir is normally some type of polymer matrix such as a polyvinylpyrrolidone or a silicone polymer from which the drug is slowly released. A microporous membrane such as a polypropylene film may serve as a membrane to control the rate of release.

The compounds may be used in association with other therapeutic agents including, for example, antibiotics or antiviral agents.

The physician or veterinarian in attendance will determine the optimum dosage in consideration of such factors as age, weight and general health of the subject. A dose which will be effective to stimulate the desired response will normally be from about 100 to 600 mg/kg body weight, although wide variations are possible. The dosage may be administered in one treatment, in several treatments given over a period of time, or over an extended period of time in transdermal or other sustained release preparation.

The following examples are given solely for the purpose of illustration and are not to be construed as limitations of this invention, many apparent variations of which are possible without departing from the spirit or scope thereof.

EXAMPLE 1

93 g 2-methyl-2,5-dimethoxy-dihydrofuran (N. Clauson-Kaas and F. Lindborg (1947) Acta Chem. Scand. 1: 619. was added under vigorous mechanical stirring to a solution of 75 g L-ascorbic acid in 750 ml water at room temperature. The furan was used in 50% excess. The solution became homogenous within 15-20 minutes. The reaction was monitored by a high pressure liquid chromograph equipped with a UV detector. The original peak of Rf 1.6 of L-ascorbic acid at 254 nm in 20% aqueous methanol disappeared while a new peak appeared at Rf 5.9 to 6.0, under 64 atmospheres. It was simultaneously observed that the solution did not consume any more iodine which is indicative of the total disappearance of L-ascorbic acid.

After standing overnight at 20° C. the aqueous solution was freeze-dried to give a pale yellow foam. The latter showed well defined IR, $^{13}$C NMR and $^1$H NMR spectra.

Next, 64.0 g (0.25M) of the crude product (melting point 55° C.) and 25.0 g (0.25M) of succinic anhydride were placed into a 1 liter round-bottomed flask equipped with a reflux condenser and a nitrogen inlet tube. After adding 200 ml of HPLC-grade ethyl acetate, the reaction mixture was refluxed for 4 hours. The homogeneous solution was cooled to room temperature and then placed in an ice-water bath. A white precipitate formed which was filtered by suction and washed with a few ml of cold ethyl acetate to give 29.9 g of the crude product (yield 46.6%). The filtrate was concentrated to half volume and cooled in an ice-water bath. The second crop of precipitate was again filtered to give 13.5 g of solid which contained some unreacted succinic anhydride.

The product was recrystallized from a solvent mixture (ethyl acetate/chloroform: 20/80) to give a total yield of 22.5 g (yield 35.2%) of pure product (long white needles-melting point 134°-134.5° C.)

Analysis: Calculated for $C_{26}H_{28}O_{17}$: C, 50.99; H, 4.61; O, 44.41. Found: C, 50.67; H, 4.52; O, 44.58.

X-ray crystallography confirmed the structure of the compound and showed the presence of 2:1, 2-furyl-butyrolactone: succinic anhydride, molecular complex in a unit cell.

EXAMPLE 2

186 g 2-methyl-2,5-dimethoxy-dihyrofuran (N. Clauson-Kaas and F. Lindborg (1947) Acta Chem. Scand. 1: 619. was added under vigorous mechanical stirring to a solution of 150 g L-ascorbic acid in 1.5 L water at room temperature. The furan was used in 50% excess. The solution became homogenous within 15-20 minutes. The reaction was monitored by a high pressure liquid chromograph equipped with a UV detector. The original peak of Rf 1.6 of L-ascorbic acid at 254 nm in 20% aqueous methanol disappeared while a new peak appeared at Rf 5.9 to 6.0 under 64 atmospheres. It was simultaneously observed that the solution did not consume any more iodine which is indicative of the total disappearance of L-ascorbic acid.

After standing overnight at 20° C. the aqueous solution was freeze-dried to give a pale yellow foam. The latter showed well defined 1R, $^{13}$C NMR and $^1$HNMR spectra.

Next, 119.65 g (0.467 mole-assuming 100% purity) of the crude product (melting point 55° C.) were dissolved in 216 ml of HPLC grade ethyl acetate. 23.3 g succinimide (0.235 mole) were added and the mixture was stirred under positive nitrogen pressure. After a few minutes of stirring, a white solid precipitated. The reaction mixture was then heated for 30 min. in an oil bath until the solid redissolved. Heating was stopped and the solution was allowed to cool to room temperature while stirring and then in an ice water bath for 2 hours. A precipitate formed which was filtered by suction, washed with 150 ml of cold chloroform and dried under vacuum to give 67.4 g of crude product (56.3% yield.)

The product was recrystallized from a solvent mixture (ethyl acetate/chloroform: 60/40) to give a total yield of 52.2 g (yield 43.6%) of pure product (long white needles—melting point 132°-133° C.).

Analysis: Calculated for $C_{26}H_{29}NO_{16}$: C, 51.07; H, 4.78; O, 41.86; N, 2.29. Found: C, 51.17; H, 4.93; O, 41.81; N, 2.21.

X-ray crystallography, confirmed the structure of the compound and showed the presence of a 2:1, 2-furyl-butyrolactone: succinimide molecular complex in a unit cell.

EXAMPLE 3

93 g 2-methyl-2,5-dimethoxy-dihydrofuran (N. Clauson-Kaas and F. Lindborg (1947) Acta Chem. Scand. 1: 619 were added under vigorous mechanical stirring to a solution of 75 g L-ascorbic acid in 750 ml water at room temperature. The furan was used in 50% excess. The solution became homogenous within 15–20 minutes. The reaction was monitored by a high pressure liquid chromograph equipped with a UV detector. The original peak of Rf 1.6 of L-ascorbic acid at 254 nm in 20% aqueous methanol disappeared while a new peak appeared at Rf 5.9 to 6.0, under 64 atmospheres. It was simultaneously observed that the solution did not consume any nore iodine which is indicative of the total disappearance of L-ascorbic acid.

After standing overnight at 20° C. the aqueous solution was freeze-dried to give a pale yellow foam. The latter showed well defined IR, $^{13}C$ NMR and $^{1}H$ NMR spectra.

Next, 10.24 g (0.04M) of the crude product (melting point 55° C.) and 2.5 g (0.22M) of N-methylsuccinimide were placed into a 1 liter round-bottomed flask equipped with a reflux condenser and a nitrogen inlet tube. After adding 20 ml of HPLC-grade ethyl acetate, the reaction mixture was refluxed for 4 hours. The homogeneous solution was cooled to room temperature and then placed in an ice-water bath. A white precipitate formed which was filtered by suction and washed with a few ml of cold ethyl acetate to give 5.20 g of the crude product (yield 50.8%). The filtrate was concentrated to half volume and cooled in an ice-water bath.

The product was recrystallized from a solvent mixture (ethyl acetate/chloroform: 1/1) to give a total yield of 3.21 g (yield 31.3%) of pure product (long white needles—melting point 105°–106.5° C.).

Analysis: Calculated for $C_{27}H_{31}NO_{16}$: C, 51.84; H, 5.00; N, 2.24; O, 40.92. Found: C, 51.98; H, 5.12; N, 2.08; O 40.63.

X-ray crystallography confirmed the structure of the compound and showed the presence of a 2:1, 2-furyl-butyrolactone:N-methylsuccinimide molecular complex in a unit cell.

EXAMPLE 4

PREPARATION OF MTMFBL

Preparation of 2-methylthiomethyl furan

Finely powdered potassium hydroxide (19.97 g, 0.355 mole) was added portionwise to a cold mixture of furfuryl mercaptan (40.0 g, 0.350 mole) and iodomethane (49.72 g, 0.350 mole). The reaction mixture was allowed to stir for 6 hours and 36 mL of water were added. The solution was extracted with ether (3×300 mL) and the combined organic fractions were dried over anhydrous sodium carbonate. After the removal of the solvent, the residue was distilled under reduce pressure to give 15.0 g (34%) colorless product, bp 61° C. (20 mm Hg), $n^{22}=1.5210$.

Prepration of 2-methylthiomethyl-2,5-dimethoxy-2,5-dihydro furan

A mixture of 2-methylthiomethyl furan (23.3 g, 0.182 mole), anhydrous sodium carbonate (32.16 g, 0.303 mole), methylene chloride (40 mL) and absolute methanol (40 mL) was cooled to $-20°$ C. under nitrogen atmosphere. A solution of bromine (24.32 g, 0.152 mole) in 60 mL absolute methanol was added over a period of one hour. The reaction mixture was stirred for another 4 hours and filtered by suction. The filtrate was stirred with anhydrous potassium carbonate (10 g-1 hour) and filtered. The solvents were removed on the rotary evaporator and methylene chloride (100 mL) was added. The organic solution was dried over anhydrous sodium sulfate, filtered and the solvent was removed on the rotary evaporator. The residue was distilled under reduced pressure to give 16.51 g (57%) of pure product, bp 66°–68° C. (0.4 nm Hg), $n^{23}=1.4860$.

Preparation of 2-(5-methylthiomethyl-2-furyl)-2-hydroxy-3-keto4-dihydroxyethyl-butyrolactone (MTMFBL)

L-ascorbic acid (8.8 g, 0.05 mole) was dissolved in 62 mL water that had been purged with nitrogen for 1 hour. Freshly distilled 2-methylthiomethyl-2,5-dimethoxy-2,5-dihydrofuran, the insoluble droplets were removed by treatment with methylene chloride. The aqueous fraction was frozen and freeze-dried to give 14.2 g (98%) crude product. The amorphous solid was dissolved in 100 mL ethyl acetate and was shaken with 3 g decolorizing charcoal and 3 g celite. After filtration, the solvent was removed under vacuum to give 12.7 g (88%) amorphous product, sinters 40°–42° C.

EXAMPLE 5

PREPARATION OF MMFBL

Preparation of 2-methoxymethyl furan

Furfuryl alcohol (225 mL, 2.6 mole) and iodomethane (162 mL, 2.6 mole) were placed in a 1 L three-necked flask equipped with a mechanical stirrer and a reflux condenser. To the cold ($-10°$ C.) mixture was added in small portions powdered potassium hydroxide (148 g, 2.6 mole). After the addition of KOH, the reaction mixture was stirred for 6 hours at ambient temperature. Cold water (200 mL) was added and the organic fraction was extracted with ether (3×300 mL). The ether extract was dried (anhydrous $Na_2SO_4$) and the solvent evaporated. Distillation of the crude product gave 193 g (66%) of the desired compound (bp 130°–134°) as a colorless liquid.

Preparation of 2-methoxymethyl-2,5-dimethoxy-2,5-dihydrofuran

2-Methoxymethyl furan (120.4 g, 1.07 moles), anhydrous methanol (250 ml, 6.18 moles), anhydrous sodium carbonate (190 g), and methylene chloride (250 ml) were placed in a 3L three-necked flask equipped with a mechanical stirrer and an addition funnel. The mixture was cooled to $-10°$ to $-15°$ C. and an ice-cold solution of bromine (53 ml, 1.04 moles) in 500 ml anhydrous methanol was added dropwise with stirring. Four hours after the addition of the bromine solution, the mixture was filtered by suction. The excess solvent was removed on a rotatory evaporator and the crude product was distilled under reduced pressure to give colorless 2-methoxymethyl-2,5-dimethoxy-2,5-dihydrofuran (118.3 g, 65%), bp. 57°–58° C. (0.2 mm Hg), $n^{21} - 1.4414$.

Preparation of 2-(methoxymethyl-2-furyl)-2-hydroxy-3-keto-4-dihydroxyethylbutyrolactone (MMFBL)

Distilled water (375 mL) was degassed for 1.5 hours in a three-necked 1 L flask equipped with a magnetic stirring bar. L-Ascorbic acid (75.0 g) was added and to the resulting solution was added 2-methoxymethyl-2,5-dimethoxy-2,5-dihydrofuran (74.9 g) dropwise with stirring over a period of 1 hour. Four hours after the end of the addition, the reaction mixture was frozen and partially evacuated on a Virtis Freezemobile. Sixty-five hours later, the liquefied reaction mixture was again frozen and freeze-dried at 10–15 millitorr for at least one week to give the desired product (117.84 g).

EXAMPLE 6

This example illustrates some of the typical formulations utilized in the practice of this invention.

| A Tablet Formulation | |
|---|---|
| Formula: | Mg/tablet |
| MTMFBL | 200.00 |
| Citric acid | 1.00 |
| Lactose | 33.00 |
| Diacalcium phosphate | 70.00 |
| Pluronic, F-68 | 30.00 |
| Sodium Lauryl Sulfate | 15.00 |
| Polyvinylpyrrolidone | 15.00 |
| Carbowax 1500 | 5.00 |
| 3A alcohol 50 ml./1000 tablets | |
| Corn Starch | 30.00 |
| Dry: | |
| Sodium Lauryl Sulfate | 3.00 |
| Magnesium stearate | 3.00 |
| TOTAL WEIGHT | 350.00 |

Procedure.

Mix together the MTMFBL, citric acid, Pluronic F-68, sodium lauryl sulfate, lactose and diacalcium phosphate. Screen through No. 60 mesh screen. Granulate the screened mix with an alcoholic solution containing the polyvinylpyrrolidone, Carbowax 1500 and 6000. Add additional alcohol, if necessary, to bring powder mix to a pasty mass. Add corn starch and continue mixing until uniform damp granules are formed. Pass the damp granulation through a No. 10 screen and dry in an oven at 100° C. for about 4 hours. Screen the dried granulation using a No. 16 screen, add sodium lauryl sulfate and magnesium stearate, mix and compress on a tablet machine to specifications.

Similar tablets are prepared with MMFBL.

| B Capsule Formation | |
|---|---|
| Formula: | Mg./capsule |
| MTMFBL | 100.00 |
| Citric acid | 100.00 |
| Pluronic F-68 | 40.00 |
| Sodium lauryl sulfate | 20.00 |
| Lactose | 238.00 |
| Magnesium stearate | 1.00 |

Procedure.

Mix together the MTMFBL, citric acid, Pluronic F-68, sodium lauryl sulfate and lactose. Pass through a No. 80 screen. Add the magnesium stearate, mix and encapsulate into the proper size 2-piece gelatin capsule.

Similar capsules are prepared with MMFBL.

| C Parenteral Formulation | | |
|---|---|---|
| Formula: | | |
| MTMFBL B | mg/10 ml | 200 |
| Benzyl alcohol, UF | mg/10 ml | 50.0 |
| Methyl paraben, USP | mg/10 ml | 18.0 |
| Propyl paraben, USP | mg/10 ml | 2.0 |
| Water | ml | 10 |

Procedure.

Dissolve the parabens in approximately 8.5 ml of water at 60° to 70° C. Cool the solution to 40° C. and add the benzyl alcohol. Cool the resultant solution to room temperature and add the MTMFBL. Place the suspension in a sterile receptacle. Fill suitably sized vials cap loosely and autoclave for one-half hour at 110° C. (15 p.s.i.g.). Each milliliter of this formulation delivers 20 mgs. of active compound.

Parenteral formulations containing MMFBL are similarly prepared.

What is claimed is:

1. A method of treating inflammation in a mammal in need of such treatment which comprises administration to said mammal of an antiinflammatory amount of a compound selected from the group represented by the formulas:

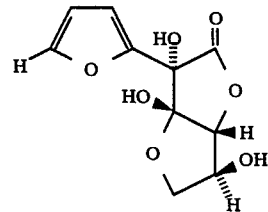

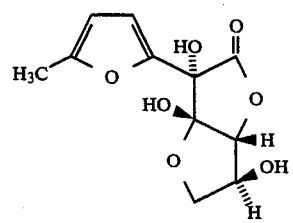

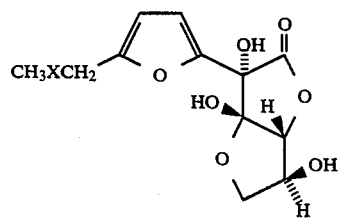

-continued

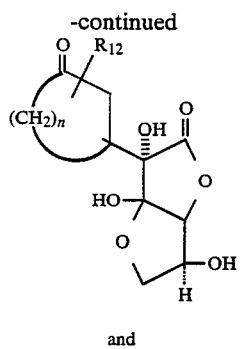

and

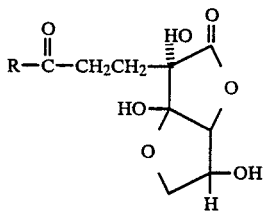

wherein x is sulfur or oxygen; R is lower alkyl; n is 2, 3, or 4; $R_{12}$ is hydrogen, lower alkyl, or lower haloalkyl.

2. A method as in claim 1 wherein the compound is represented by the formula:

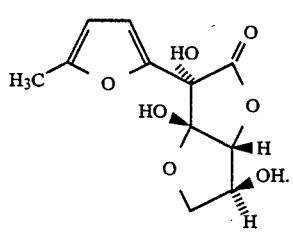

3. A method as in claim 1 wherein the compound is represented by the formula:

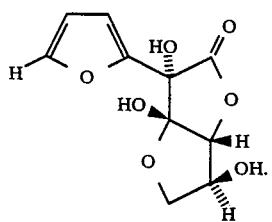

4. A method as in claim 1 wherein the compound is represented by the formula:

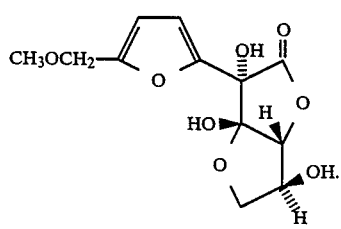

5. A method as in claim 1 wherein the compound is represented by the formula:

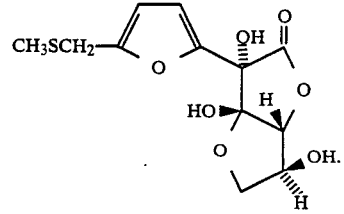

6. A method as in claim 1 wherein the compound is represented by the formula:

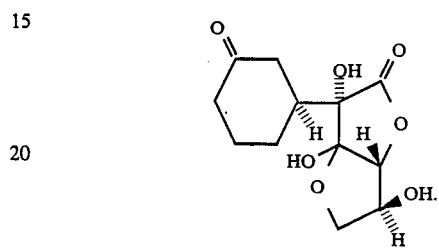

7. A method as in claim 1 wherein the compound is represented by the formula:

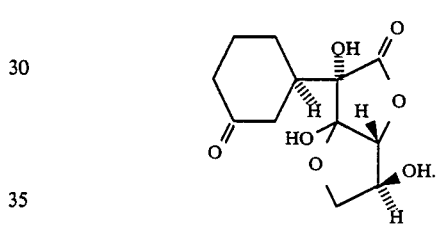

8. A method as in claim 1 wherein the compound is represented by the formula:

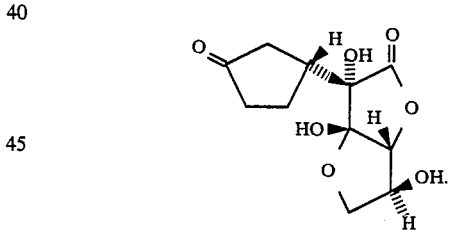

9. A method as in claim 1 wherein the compound is represented by the formula:

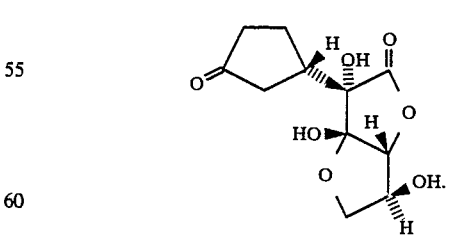

10. A method as in claim 1, 2, 3, 4, 5, 6, 7, 8 or 9 wherein the mammal is an animal.

11. A method as in claim 1, 2, 3, 4, 5, 6, 7, 8 or 9 wherein the mammal is a human.

* * * * *